US009814791B2

(12) United States Patent
Cutler et al.

(10) Patent No.: US 9,814,791 B2
(45) Date of Patent: Nov. 14, 2017

(54) BIO-COMPATIBLE RADIOPAQUE DENTAL FILLERS FOR IMAGING

(71) Applicants: Augusta University Research Institute, Inc., Augusta, GA (US); Georgia Tech Research Corporation, Atlanta, GA (US)

(72) Inventors: Christopher Cutler, Martinez, GA (US); Kenneth H. Sandhage, Roswell, GA (US)

(73) Assignees: Augusta University Research Institute, Inc., Augusta, GA (US); Georgia Tech Research Corporation, Atlanta, GA (US)

( * ) Notice: Subject to any disclaimer, the term of this patent is extended or adjusted under 35 U.S.C. 154(b) by 173 days.

(21) Appl. No.: 14/789,584

(22) Filed: Jul. 1, 2015

(65) Prior Publication Data

US 2016/0000939 A1 Jan. 7, 2016

Related U.S. Application Data

(60) Provisional application No. 62/019,503, filed on Jul. 1, 2014, provisional application No. 62/060,188, filed on Oct. 6, 2014.

(51) Int. Cl.
A61B 6/14 (2006.01)
A61K 49/04 (2006.01)
(Continued)

(52) U.S. Cl.
CPC .......... *A61K 49/0414* (2013.01); *A61B 6/032* (2013.01); *A61B 6/145* (2013.01); *A61B 6/466* (2013.01); *A61B 6/481* (2013.01)

(58) Field of Classification Search
CPC .......... A61B 6/032; A61B 6/145; A61B 6/466; A61B 6/481; A61K 31/337; A61K 31/454;
(Continued)

(56) References Cited

U.S. PATENT DOCUMENTS 4,149,083 A * 4/1979 Suys .............. G21K 4/00
250/486.1
5,570,182 A 10/1996 Nathel
(Continued)

FOREIGN PATENT DOCUMENTS

| EP | 1977768 | 10/2008 |
|---|---|---|
| WO | 2007126411 | 2/2007 |
| WO | 2012007567 | 1/2012 |

OTHER PUBLICATIONS

Sulawan Kaowphonga, Titipun Thongtemb and Somchai Thongtemc.Effect of solvents on the microstructure of CaWO4 prepared by a solvothermalsynthesis. Journal of Ceramic Processing Research. vol. 11, No. 4, pp. 432-436 (2010).*
(Continued)

*Primary Examiner* — Irakli Kiknadze
(74) *Attorney, Agent, or Firm* — Smith, Gambrell & Russell, LLP; Charles Vorndran

(57) ABSTRACT

Dental contrast formulations ("fillers") of tailorable X-Ray radiopacity and methods for their use are provided. The disclosed fillers include mixtures of solid particles suspended in a biocompatible fluid. The solid particles contain one or more X-ray radiopaque materials. The biocompatible fluid can also contain one or more soluble X-ray radiopaque components. By controlling the composition of the solid particles, the composition of the biocompatible fluid, and the loading of the solid particles in the biocompatible fluid, the X-ray radiopacity and stability of the filler can be tailored to allow for improved discrimination of the filler within peri-
(Continued)

odontal pockets, relative to adjacent soft tissue and teeth, so that the 3-D shape, volume, and depth of the pocket can be precisely and rapidly determined by X-Ray imaging.

4 Claims, 7 Drawing Sheets

(51) Int. Cl.
  *A61B 6/03* (2006.01)
  *A61B 6/00* (2006.01)
(58) Field of Classification Search
  CPC .. A61K 49/0414; A61K 6/083; A61K 6/0023; A61K 6/0017; A61K 6/09; A61K 6/087; A61K 6/0038; A61K 6/002; A61K 6/0008; A61K 6/0835; A61K 6/0073; A61K 6/0091; A61K 6/0276; A61K 6/005; A61K 6/0088; A61K 6/024; A61K 6/0029; A61K 6/0215; G01N 2333/70578; G01N 2800/50; G01N 2800/52; G01N 33/57415
  USPC .............................. 378/38, 54; 523/117, 115
  See application file for complete search history.

(56) References Cited

U.S. PATENT DOCUMENTS

| | | | |
|---|---|---|---|
| 6,471,993 B1 | 10/2002 | Shastri | |
| 6,572,693 B1* | 6/2003 | Wu | A61K 6/0017 106/35 |
| 6,953,594 B2 | 10/2005 | Lee | |
| 7,473,417 B2 | 1/2009 | Zeltinger | |
| 7,514,249 B2 | 4/2009 | Gower | |
| 8,153,591 B2 | 4/2012 | Masters | |
| 8,252,851 B2 | 8/2012 | Young | |
| 8,613,938 B2 | 12/2013 | Akella | |
| 2002/0137812 A1 | 9/2002 | Chow | |
| 2003/0180344 A1 | 9/2003 | Wise | |
| 2005/0191248 A1 | 9/2005 | Hunter | |
| 2006/0046226 A1 | 3/2006 | Bergler | |
| 2010/0041789 A1 | 2/2010 | Neffgen | |
| 2011/0142810 A1 | 6/2011 | Saito | |
| 2011/0182995 A1* | 7/2011 | Asgary | A61O 5/50 424/489 |
| 2013/0224690 A1 | 8/2013 | Karlinsey | |
| 2014/0050669 A1 | 2/2014 | Benn | |
| 2015/0265371 A1 | 9/2015 | Kim | |

OTHER PUBLICATIONS

Boyle, et al., "Synthesis and characterization of solvothermal processed calcium tungstate nanomaterials from alkoxide precursors", Chem Mater., 26:965-75 (2014).
Pinto, et al., "Electrostatic assembly and growth of gold nanoparticies in cellulosic fibers", J Colloid Interface Sci., 312:506-12 (2007).
International Search Report for PXCT Application PCT/US2015/038860.
Cho, et al., "Thermorheologic Properties of Aqueous Solutions and Gels of Poloxamer 407," Drug Dev. Ind. Pharm., 13:1227-32 (1997).
Collares, et al., "Nanostructured hydroxyapatite as filler for methacrylate-based root canal sealers," Int Endod J 45:63-67 (2012).
Cornelio, et al., "Cytotoxicity of Portland Cement with Different Radiopacifying Agents: A Cell Death Study," J. Endodontics 37:203-10 (2011).
Diamanti, et al., "Anodic oxidation of titanium: from technical aspects to biomedical applications," J Appl Biomater Biomech 9:55-69 (2011).
Duarte, et al., "influence of calcium hydroxide association on the physical properties of AH Plus," Journal of endodontics 36:1048-51 (2010).
Ganss, et al., "Efficacy of the stannous ion and a biopolymer in toothpastes on enamel erosion/abrasion," J. Dent., 40:1036-43 (2012).
Garrett, et al., "The effect of a bioresorbable matrix barrier in endodontic surgery on the rate of periapical healing: an in vivo study", J Endod., 28(7);503-6 (2002).
Gittens, et al., The roles of titanium surface micro/nanotopography and wettability on the differential response of human osteoblast lineage cells. Acta Biomater 9:6268-77 (2013).
Goff, et al., Gelling of cellulose nanowhiskers in aqueous suspension J. Appl. Polym. Sci, 131(17):DOI:10.1002/APP.40676 (2014).
Hasani, et al, "Correction: Cationic surface functionalization of cellulose nanocrystals", Soft Matter, 4:2238-44 (2008).
Hulvert, et al., "Tissue Reaction to Three Ceramics of Porous and Non-Porous Structures," J. Biomed. Mater. Res 6:347-74 (1972).
Kalathingal, et al., "In vitro assessment of cone beam local computed tomography for proximal caries detection.", Oral Surg. Oral Med. Oral Pathol. Oral Radial. Endod., 104:699-704 (2007).
Kurumada, et al., "Viscosity Studies of Pluronic F127 in Aqueous Solution," Prog. Colloid Polymer Sci., 123:12-15 (2004).
Liu, et al.,"The use of sodium trimetaphosphate as a biomimetic analog of matrix phosphoproteins for remineralization of artificial caries-like dentin", Dent. Mater., 27:465-77 2011).
Ohtsu, et al., "Calcium-Hydroxide Slurry Processing for Bioactive Calcium-Titanate Coating on Titanium," Surf. Coatings Technol. 202:5110-5 (2008).
Prud\Homme, et al., "Structure and Rheology Studies of Poly(oxyethylene-osypropylene-oxyethylene) Aqueous Solution," Langmuir, 12:4651-59 (1996).
Rodriguez, et al., "Effect of CaTiO(3)-CaCO(3) prepared by alkoxide method on cell response," J Biomed Mater Res A 93:297-303 (2010).
Schmolka, "Artificial skin. I. Preparation and properties of pluronic F-127 gels for treatment of burns," J. Biomed. Mater. Res., 6:571-82 (1972).
Sollazzo, et al., "Zirconium oxide coating improves implant osseointegration in vivo," Dent Mater 24:357-61 (2008).
Tasdemir, et al., "Evaluation of the radiopacity of new root canal paste/sealers by digital radiography," Journal of endodontics., 34:1388-90 (2008).
Wang, et al., "Kinetics of Sol-to-Gel Transition for Poloxamer Polyols," J. Appl. Polymer Sci., 43:283-92 (1991).
Wang, et al., "Phase Composition and in-vitro Bioactivity of Plasma Sprayed Calcia Stabilized Zirconia Coatings," Surf. Coatings Technol., 202:5824-31 (2008).
Yamaguchi, S., et al., "Formation of a bioactive calcium titanate layer on gum metal by chemical treatment," J Mater Sci Mater Med., 23:873-83 (2012).

* cited by examiner

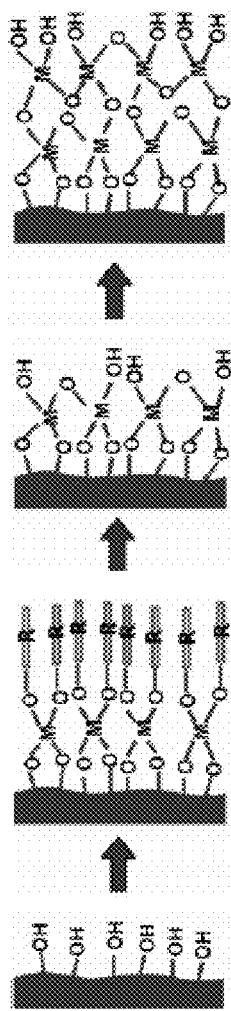

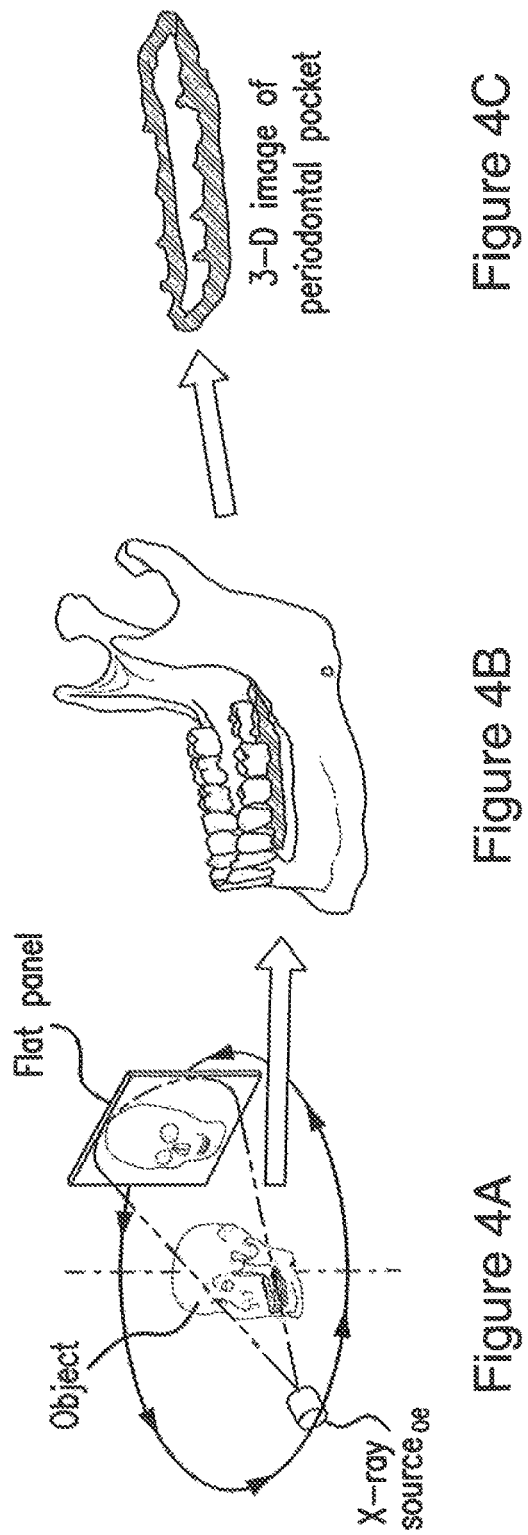

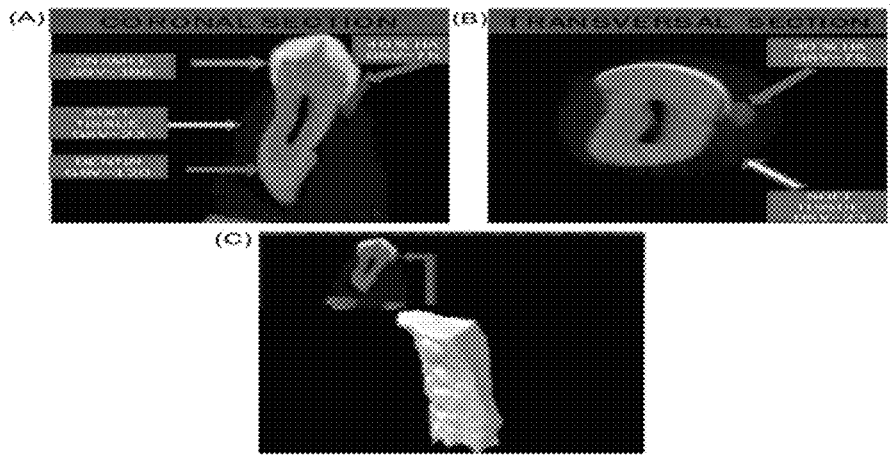
FIGS. 5A-5C
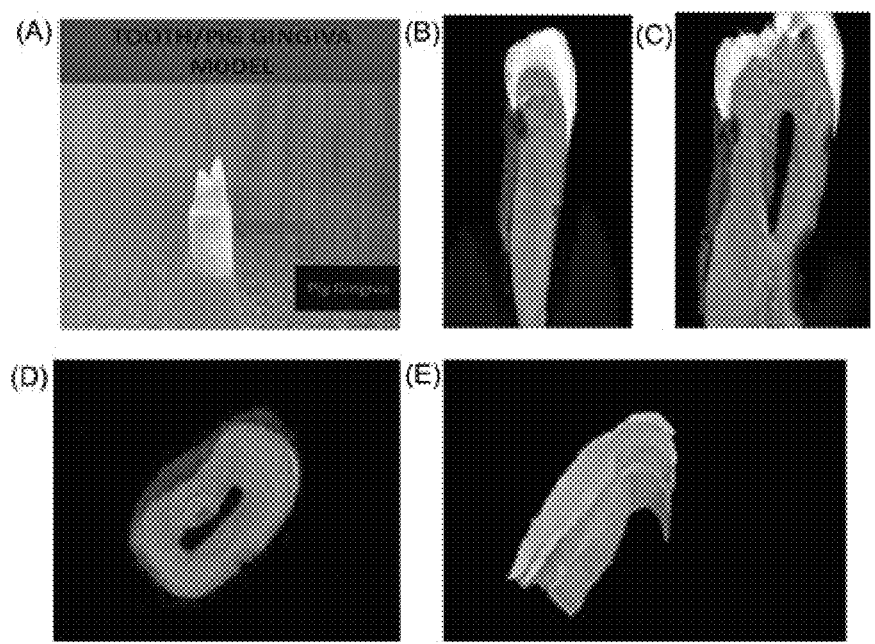
FIGS. 6A-E

BIO-COMPATIBLE RADIOPAQUE DENTAL FILLERS FOR IMAGING

CROSS REFERENCE TO RELATED APPLICATIONS

This application claims benefit of and priority to U.S. Provisional Patent Application No. 62/019,503 filed on Jul. 1, 2014, and to U.S. Provisional Patent Application No. 62/060,188 filed Oct. 6, 2014, both of which are incorporated by reference in their entireties.

FIELD OF THE INVENTION

The present disclosure relates generally to compositions and methods for dental imaging, and more particularly, to three-dimensional imaging of periodontal pockets.

BACKGROUND OF THE INVENTION

Periodontal disease (or periodontitis) is a set of inflammatory diseases affecting the periodontium, which are the tissues that surround and support the teeth. Periodontitis affects nearly 50% of the U.S. population and is a risk factor for cardiovascular disease. It involves progressive loss of the alveolar bone around the teeth, and if left untreated, can lead to the loosening and subsequent loss of teeth. Periodontitis is caused by microorganisms that adhere to and grow on the tooth's surfaces, and is exacerbated by an over-aggressive immune response against these microorganisms. A diagnosis of periodontitis is established by radiographic examination and by inspecting the soft gum tissues around the teeth with a probe to determine the amount of bone loss around the teeth.

Bone loss leading to periodontitis is preceded by soft tissue detachment from the teeth, and subsequent formation of pockets around the affected teeth ranging in depth from 4-10 mm. One of the hallmarks of successful therapy for periodontitis is resumption of healthy pocket depths of 1-3 mm. The method used to measure the depth of the pockets before and after therapy has remained relatively unchanged for over 75 years. The dentist inserts a thin metal periodontal probe, marked in mm, at 6 sites around each tooth between the tooth and gum until the probe stops. This diagnostic procedure, called periodontal probing, is uncomfortable for the patient. The probing depth numbers are recorded by an assistant, yielding 192 numbers per visit for a patient with complete dentition. To these numbers are added the level of gingival recession, recorded from the edge of the gingiva to the cement-enamel junction (CEJ), to determine the attachment loss around these 192 sites per patient, for a total of 384 readings per patient visit. The pressure exerted during probing by different dentists and at different appointments can differ considerably, inadvertently leading to variability in recorded numbers. Overall, this important oral health care procedure is time consuming, requires two operators, is variable, and is uncomfortable to the patient. New methods for measuring the depth of dental pockets are needed.

Therefore, it is an object of the invention to provide a method of imaging pockets between teeth and soft tissue, that is appreciably more precise, reproducible, rapid, and less labor intensive than traditional periodontal probing.

It is another object of the invention to provide dental filler formulations of tailorable radiopacity.

It is another object of the invention to provide a method of imaging pockets between teeth and soft tissue that is painless to the patient.

It is another object of the invention to provide three-dimensional images of the shapes and volumes of pockets for more accurate diagnoses and assessments of treatments.

It is another object of the invention to provide dental filler formulations that are anti-microbial or anti-inflammatory.

It is another object of the invention to provide dental filler formulations that are therapeutic with regards to periodontitis or peri-implantitis.

SUMMARY OF THE INVENTION

Dental contrast formulations of tailorable X-Ray radiopacity and methods for their use are described. One embodiment provides formulations containing solid particles dispersed in a biocompatible fluid. By controlling the composition of the solid particles, the composition of the biocompatible fluid, and the loading of the solid particles in the biocompatible fluid, the X-ray radiopacity of the formulation (also referred to as "filler") can be tailored to allow for improved discrimination of the filler within periodontal pockets, relative to adjacent soft tissue and teeth, so that the 3-D shape, volume, and depth of the pocket can be accurately and rapidly determined by X-Ray imaging. In a preferred embodiment, the X-ray radiopacity of the filler is tailored to be greater than that of soft tissue. One embodiment provides a filler having an X-ray radiopacity tailored to be between that of soft tissue and that of dentin. Another embodiment provides a filler in which the X-ray radiopacity is tailored to be greater than that of dentin. Still another embodiment provides a filler in which the X-ray radiopacity is tailored to be between that of dentin and that of enamel. Yet another embodiment provides a filler in which the X-ray radiopacity is tailored to be greater than that of enamel.

Certain embodiments provide fillers in which the solid particles of the filler include one or more materials with X-ray radiopacity between that of soft tissue and that of dentin. Another embodiment provides a filler having solid particles that include one or more materials with X-ray radiopacity greater than that of dentin. Still another embodiment provides a filler having solid particles that include of one or more materials with X-ray radiopacity between that of dentin and that of enamel. Yet another embodiment provides a filler having solid particles that include of one or more materials with X-ray radiopacity greater than that of enamel.

The solid particles of the filler can include one or more X-ray radiopaque inorganic compounds. Alternatively, the solid particles of the filler include one or more oxide compounds. In some embodiments, the solid particles of the filler include one or more calcium-bearing compounds. The calcium-bearing compounds can be one or more of the following: $CaWO_4$, $Ca_3WO_6$, $CaZrO_3$, $CaTiO_3$, $Ca_3Ti_2O_7$, $Ca_4Ti_3O_{10}$, $Ca_3P_2O_8$, and $Ca_{10}(PO_4)_6(OH)_2$.

As noted above, the X-ray radiopaque component is combined with a biocompatible fluid. In a preferred embodiment, the X-ray radiopaque component is mixed with, suspended in, or dissolved in the biocompatible fluid. One embodiment provides a composition containing a biocompatible fluid and a soluble X-ray radiopaque component having an X-ray radiopacity between that of soft tissue and that of dentin. The biocompatible fluid containing the soluble X-ray radiopaque component can have: (1) an X-ray radiopacity greater than that of dentin; (2) an X-ray radiopacity between that of dentin and that of enamel; or an X-ray radiopacity greater than that of enamel.

The soluble X-ray radiopaque component in the biocompatible fluid can contain iodine or an iodine-bearing molecule or both. One embodiment provides a composition in which the soluble X-ray radiopaque component is an iodide salt dissolved in the biocompatible fluid. In some embodiments, the soluble X-ray radiopaque component is sodium iodide dissolved in the biocompatible fluid. In some embodiments, the soluble X-ray radiopaque component in the biocompatible fluid consists of an iodine anion.

The solid particles in the filler can include an X-ray radiopaque inorganic compound that is a coating deposited on a template in the form of a particle. The template can be a spherical particle or a non-spherical particle. In another embodiment, the template is an organic particle. The organic template particle can include nanocellulose. In another embodiment, the organic template particle is a cellulose nanofiber (also called microfibrillated cellulose). In another embodiment, the organic template particle is or contains nanocrystalline cellulose, bacterial nanocellulose, or both. In another embodiment, the template is an inorganic particle. In another embodiment, the template is a biogenic inorganic particle. The biogenic inorganic particle template can be the $SiO_2$ microshell of a diatom. In another embodiment, the template is a synthetic inorganic particle.

The solid particles in the filler can contain porosity so as to allow for the incorporation of one or more therapeutic agents. Therapeutic agents include, but are not limited to anti-microbial agents, anti-inflammatory agents, anti-fungal agents, or combinations thereof. A preferred anti-microbial agent is an antibiotic. The therapeutic agents are typically useful for treating periodontitis, peri-implantitis, or both. In some embodiments, the porous solid particles in the filler are hollow. In some embodiments, the hollow solid particles in the filler contain walls that are porous.

One embodiment provides a composition in which the biocompatible fluid in the filler possesses a higher viscosity than water so as to inhibit settling of the solid particles relative to water, and thereby enhance the stability of the suspension of the solid particles in the biocompatible fluid relative to the stability of the suspension of solid particles in water. For embodiments in which the solid particles of the filler include or are an X-ray radiopaque material, an inhibition of the settling of the solid particles is desired in order to retain uniform radiopacity of the filler during imaging.

The biocompatible fluid in the filler can be a liquid solution containing water. The water-bearing biocompatible liquid in the filler can contain an additive to increase the viscosity of the water-bearing biocompatible liquid beyond the viscosity of water. One embodiment provides a composition in which the biocompatible fluid in the filler is a glycerol-water solution.

Another embodiment provides a composition in which the biocompatible fluid in the filler is a gel-forming solution. The gel-forming solution can contain water. Other embodiments provide a composition in which the gel-forming solution contains an organic material that causes the solution to exhibit reversible thermal gelation. In some embodiments, the organic material is a block co-polymer. Representative block co-polymers include, but are not limited to poloxamer (a polyoxyethylene, polyoxypropylene block co-polymer). In some embodiments, the poloxamer is poloxamer 407 (P-407).

Other embodiment provide compositions in which the biocompatible fluid is a mixture of liquids. The mixture of liquids can contain water. In some embodiments, the biocompatible fluid in the filler is a mixture of liquids in which at least one of the liquids contains glycerol. In some embodiments, the biocompatible fluid in the filler is a mixture of liquids in which at least one of the liquids contains a gel-forming solution.

One embodiment provides a composition in which the biocompatible fluid in the filler is a thixotropic fluid. The thixotropic biocompatible fluid can be a mixture containing a liquid and solid particles. The thixotropic biocompatible fluid mixture can contain cellulose, microcrystalline cellulose, nanocellulose, cellulose nanofibers (also called microfibrillated cellulose), nanocrystalline cellulose, bacterial nanocellulose, and combinations thereof.

The settling rate of the particles in the filler can be reduced by tailoring one or more of the following: the average size of the solid particles, the surface roughness of the solid particles, the shape of the solid particles, and the porosity of the solid particles in the filler. One embodiment provides a composition containing solid particles formed of a coating on a core material, with the composition, size, and density of the core material tailored to reduce the settling rate of the solid particles in the filler.

BRIEF DESCRIPTION OF THE DRAWINGS

The following figures are provided for the purpose of illustration only and are not intended to be limiting.

FIG. 1A reveals a periapical intraoral (2-D) dental X-ray of teeth and bone. FIG. 1B reveals 2-D dental X-ray (50 kV) images of initial nhydroxyapatite prototypes and controls (mouse gingiva and bone) in wells (red arrows). FIG. 1C reveals MicroCT results in gray scale value (GSV). FIG. 1D reveals the radiopacity of different oxide particles drawn into sealed micropipettes (blue bracket) at 0.2 mm and 0.5 mm thickness. FIG. 1E shows a tooth/gingival analogue with probing depth. FIG. 1F shows a pig jaw pocket analogue.

FIGS. 2A, 2B, 2C, and 2D are schematics showing the steps or stages of the layer-by-layer surface sol-gel process. The substrate contains a high density of hydroxyl groups (FIG. 2A). Exposure of such hydroxyl groups to a metal alkoxide results in the formation of metal-oxygen bonds (FIG. 2B) and alcohol (not shown) as reaction products. Once a monolayer is deposited, the pendant, unreacted alkoxide (OR) groups may be exposed to water to regenerate bound hydroxyl (OH) groups (FIG. 2C) (and alcohol product molecules). Repeated, alternating exposure to solutions of metal alkoxide and then water can be used to build up, in a layer-by-layer fashion, oxide layers of desired thickness (FIG. 2D).

FIGS. 4A, 4B, and 4C are an illustration of the disclosed methods. Periodontal pockets within a human skull will be loaded with filler suspension material (FIG. 4B). A series of cone beam CT analyses can be used to generate a 3-D, digitally-reconstructed image of the filled periodontal pockets (FIG. 4A). It is expected that such a 3-D image will appear as a continuous ribbon around the teeth (FIG. 4C).

FIGS. 5A, 5B and 5C are three dimensional renderings by MicroCT of hydroxyapatite particles in glycerol of the tooth/gingival analogue model in FIG. 1. In FIG. 5A Skyscan v. 1174 MicroCT used here to image an early HA prototype (40% HA in glycerol and water), revealing a radiopacity (gray scale value [GSV]=75) that is intermediate between tooth enamel (GSV=188), and soft "tissue" (GSV=23) (FIG. 5A, 5B). The filler-bearing radiopaque "pockets" were then be "reassembled" in 3-D using CT analyzer v. 1.12.0.

FIG. 6A is a photograph of a human tooth/pig gingiva model. FIGS. 6B-6E are three dimensional renderings by MicroCT of hydroxyapatite in glycerol (40% wt 0.5 microns HA in 70% glycerol) injected into human tooth/pig gingiva periodontal pocket analogue FIG. 7 clearly reveal that while HA and NaI have detectable radiopacity that can be successfully imaged, calcium tungstate (CaWO4) is superior in terms of radiopacity needed to clearly delineate the pocket in the presence of highly radiopaque tooth structure; moreover, NaI, which has antimicrobial activity and radiopacity of its own may be a viable additive to impart a therapeutic value to the formulation.

DETAILED DESCRIPTION OF THE INVENTION

I. Definitions

Figures 1A, 1B, 1C, 1D, 1E, 1F:
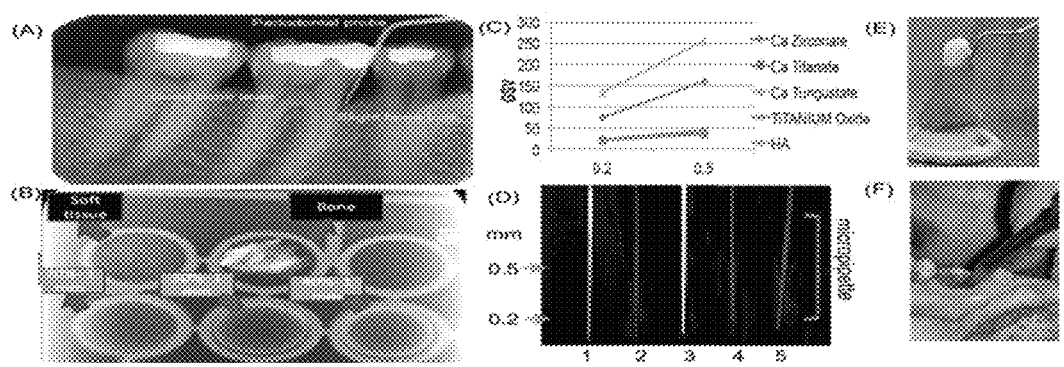
FIGS. 1A-1F show data for radiopacity testing.

Unless defined otherwise, all technical and scientific terms used in this disclosure have the same meanings as commonly understood by one of ordinary skill in the art to which this disclosure belongs.

The term "alveolar bone" or "alveolar process" as used herein refers to the thickened ridge of bone that contains the tooth sockets (dental alveoli) on bones that hold teeth. In humans, the tooth-bearing bones are the maxillae and the mandible.

The term "as a function of" as described herein refers to the definition of one variable in terms of another. The statement "evaluating A as a function of B" means that if B changes, chances are that A does too.

The term "biocompatible" as described herein refers to the ability of a material to perform with an appropriate host response in a specific application, or the quality of not having toxic or injurious effects on biological systems.

The term "bioresorbable" as described herein refers to the ability of a biomaterial to be digested by or as a consequence of cellular activity, and thus dissolve or disappear in part or in whole after implantation.

The term "bur" or "dental bur" as used herein refers to a cutting tool usually of steel or other hard metal shaped into a shank and a head, for removing carious material from teeth and preparing cavities for filling.

The term "cellulose nanocrystals" or "CNCs" as described herein refers crystals with dimensions less than 1 μm containing cellulose. In one embodiment, the nanosized rod-like cellulose fibrils are produced from wood pulp.

The term "cement-enamel junction" or "CEJ" as described herein refers to an anatomical border on a tooth between the enamel, which covers the crown of a tooth, and the cementum, which covers the root of a tooth.

The term "cone beam computed tomography" or "cone beam CT" as described herein refers to a medical imaging technique consisting of X-Ray computed tomography, where the X-Rays are divergent, forming a cone.

The term "CT scan" or "CT imaging" or "X-Ray CT scan" as described herein refers to X-Ray computed tomography, a technology that uses computer-processed X-Rays to produce tomographic images (virtual slices) of specific areas of the scanned object, allowing the user to see what's inside it without cutting it open.

The term "fluid" as described herein refers to a substance that has no fixed shape and yields easily to external pressure, such as a gas or a liquid or a liquid solution or a mixture of liquid solutions.

The term "formulation" as used herein refers to a material or mixture prepared according to a particular formula.

The term "gingiva" or "gums" as described herein refers to the mucosal tissue that lies over the mandible and maxilla inside the mouth.

The term "hollow" as described herein refers to being empty, unfilled, vacant, or having nothing inside.

The term "microparticles" as described herein refers to particles ranging in size from 1.0 to 999.9 μm. These can be of any shape, such as spherical, cubical, rod-like, ellipsoidal, hemispherical, discoidal, and cylindrical.

The term "nanoparticles" refers to particles less than 1 μm, and are typically in the range of 1 nm to 999 nm.

The term "oxide" as described herein refers to a chemical compound that contains at least one oxygen atom and one other element in its chemical formula.

The term "periapical radiography" or "PA radiography" as described herein refers to X-Rays that show the entire crown and root of the teeth.

The term "periodontal pocket" as described herein refers to an unusually deep gap in the space between the gum tissue and the tooth. The pocket is measured from the height of the gum down to the base of the space, where the gum attaches to the tooth. A healthy pocket is considered to be 3 mm or less in depth and free of inflammation, bleeding, and bacterial build-up.

The term "radiopacity" as described herein refers to the capability of a substance to hinder or completely stop the passage of X-Rays, such as the ability of lead and bones to do so, thus producing a light image on film.

The term "ribbon" as described herein refers to a long narrow strip of any composition.

The term "surface sol-gel" process or "SSG" process as described herein refers to a wet chemical, layer-by-layer method for the coating of a template with a metal oxide. The method involves the reaction of a metal alkoxide dissolved in a solution with a hydroxylated surface of a template to form a metal oxide-bearing coating.

The term "solution" refers to a homogeneous volume of matter, such as a homogeneous gas or a homogeneous liquid or a homogeneous solid, in which the minor component (the solute) is uniformly distributed within the major component (the solvent).

The term "mixture" refers to two or more distinctly different volumes of matter, such as a liquid and a solid or two immiscible liquids or two immiscible solids.

The term "tailorable X-Ray radiopacity" as described herein refers to the ability to adapt, modify, or customize the degree of X-Ray absorption.

The term "total disease exposure" as described herein refers to the fact or overall condition of being affected by a disease.

II. Formulations

Dental contrast formulations of tailorable X-Ray radiopacity and methods for their use are described. The dental contrast formulations are also referred to as fillers. One embodiment provides fillers containing solid particles dispersed in a biocompatible fluid. The solid particles contain one or more X-ray radiopaque materials. The solid particles in the contrast formulations can contain the same or different X-ray radiopaque materials. One embodiment provides a contrast composition containing a biocompatible fluid that contains one or more X-ray radiopaque materials. By controlling the composition of the solid particles, the composition of the biocompatible fluid, and the loading of the solid particles in the biocompatible fluid, the X-ray radiopacity of the filler can be tailored to allow for improved discrimination of the filler within periodontal pockets, relative to adjacent soft tissue and teeth, so that the 3-D shape, volume, and depth of the pocket can be accurately and rapidly determined by X-Ray imaging.

The microparticles in the dental contrast formulations can be have a diameter of 1 micrometer to 999 micrometers. Typically the microparticles have an average diameter of about 20 µm to about 60 µm. In one embodiment, the particles have an average diameter of 5 µm to 50 µm. The particles in the dental contrast formulations can be nanoparticles in the range of 1 nm to 999 nm. Preferably, the nanoparticles are about 500 nm or less. The particles can be present in the dental contrast formulations in about 10 wt. % to about 70 wt. %, preferably from about 30 wt. % to about 50 wt. %, most preferably about 40 wt. %

For fillers containing a mixture of solid particles having one or more X-ray radiopaque materials, suspended in a biocompatible fluid, the settling of the solid particles should be inhibited in order to retain a uniform X-ray radiopacity during imaging. One embodiment provides a contrast composition or filler in which the biocompatible fluid in the filler possesses a higher viscosity than water so as to inhibit settling of the solid particles relative to water, and thereby enhance the stability of the suspension of the solid particles in the biocompatible fluid relative to the stability of the suspension of solid particles in water.

Another embodiment provides a filler composition in which the biocompatible fluid is a gel-forming fluid that exhibits reversible thermal gelation. For example, the biocompatible fluid can be a thixotropic fluid. To reduce the settling rate of the particles in the filler, one or more of the following is tailored: the average size of the solid particles in the filler, the surface roughness of the solid particles in the filler, the shape of the solid particles in the filler, and the porosity of the solid particles in the filler. In some embodiments, the solid particles containing a coating on a core material, with the composition, size, and density of the core material tailored to reduce the settling rate of the solid particles in the filler.

Two important characteristics of the filler materials are: X-ray radiopacity and suspension stability (resistance to particle settling). Established theories for X-ray absorption and particle settling can be used to guide the selection of the solid and fluid components of the fillers, as discussed in the following.

A. Selection of Radiopaque Solid Particles for Fillers

The extent of X-ray absorption by a material may be calculated by the Beer-Lambert Law:

$$1-(I_x/I_o)=\exp[-(\mu/\rho)\rho x] \qquad (1)$$

where $I_o$, $I_x$=intensity of X-rays impinging onto, and passing through, a material of thickness x, respectively; $\rho$=mass density of the material; and $\mu/\rho$=mass absorption coefficient of the material. The wavelengths of dental X-rays range from about 0.01 to 0.06 nm, with a corresponding energy (E=hc/λ) range of about 20 to 120 keV. {K. Maeda, et al., "Compton-Scattering Measurement of Diagnostic X-ray Spectrum Using High-Resolution Schottky CdTe Detector," *Med. Phys.*, 32, 1542-1547 (2005); G. Matscheko, et al., "A Compton Scattering Spectrometer for Determining X-ray Photon Energy Spectra," *Phys. Med. Biol.*, 32, 577-594 (1987); M. Yaffe, et al., "Spectroscopy of diagnostic x rays by a Compton-scatter method," *Med Phys* 3, 328-334 (1976)} For these energies, the calculated mass absorption coefficients and the relative extent of X-ray adsorption of hydroxyapatite (HA, as $Ca_{10}(PO_4)_6(OH)_2$), titania ($TiO_2$), calcium titanate ($CaTiO_3$), calcium zirconate ($CaZrO_3$), calcium tungstate ($CaWO_4$), and a solution comprised of 60 wt % NaI dissolved in 40 wt % water are shown in Table 1. {J. H. Hubbell, S. M. S. "Tables of X-Ray Mass Attenuation Coefficients and Mass Energy-Absorption Coefficients from 1 keV to 20 MeV for Elements Z=1 to 92 and 48 Additional Substances of Dosimetric Interest," in *NISTIR* 5632. *National Instute of Standards and Technology* (http://www.nist.gov/pml/data/xraycoef/index.cfm). 1996; A. F. Scott, E. J. Durham, "Studies in the Solubilities of the Soluble Electrolytes. III. The Solubilities and Densities of Saturated Solutions of the Bromides and Iodides of Sodium and Potassium between 0° and 92°," *J. Phys. Chem.*, 34, 1424 (1930); International Center on Diffraction Data, N.S., PA, USA. Theoretical oxide densities obtained from Powder Diffraction File Cards No. 00-09-432 for hydoxyapatite (HA), $Ca_{10}(PO_4)_6(OH)_2$; No. 00-021-1272 for anatase $TiO_2$; No. 00-42-0423 for $CaTiO_3$; No. 00-35-0790 for $CaZrO_3$; No. 00-41-1431 for $CaWO_4$}

Hydroxyapatite (HA, idealized composition: $Ca_{10}(PO_4)_6(OH)_2$) is the major mineral in the enamel and dentin of teeth, whereas the other oxides in Table 1 have sufficient biocompatibility as to be used, or to be considered for use, in dental applications. {J.-M. Wu, et al. "Bioactive Bioceramic Coatings: Part II. Coatings on Metallic Biomaterials., in *Metal Oxide Nanostructures and Their Applications*, ed. A. Umar, Y.-B. H., American Scientific Publishers, Stavenson Ranch, Calif., 2010; T. Kokubo, et al., *Bioactive HA Coatings by Ti Surface Activation*, Imperial College Press, London, UK, 2013; M. V. Diamanti, et al., "Anodic oxidation of titanium: from technical aspects to biomedical applications," *J Appl Biomater Biomech* 9, 55-69 (2011); R. A. Gittens, R. A., et al., "The roles of titanium surface micro/nanotopography and wettability on the differential response of human osteoblast lineage cells. *Acta Biomater* 9, 6268-

6277 (2013); S. Yamaguchi, S., et al., "Formation of a bioactive calcium titanate layer on gum metal by chemical treatment," *J Mater Sci Mater Med* 23, 873-883 (2012); N. Ohtsu, et al., "Calcium-Hydroxide Slurry Processing for Bioactive Calcium-Titanate Coating on Titanium," *Surf Coatings Technol.* 202, 5110-5115 (2008); M. Inoue, et al., "Effect of a new titanium coating material ($CaTiO_3$-aC) prepared by thermal decomposition method on osteoblastic cell response," *J Biomater Appl* 24, 657-672 (2010); A. P. Rodriguez, et al., "Effect of CaTiO(3)-CaCO(3) prepared by alkoxide method on cell response," *J Biomed Mater Res A* 93, 297-303 (2010); G. Wang, et al., "Phase Composition and in-vitro Bioactivity of Plasma Sprayed Calcia Stabilized Zirconia Coatings," *Surf. Coatings Technol.* 202, 5824-5831 (2008); S. F. Hulvert, et al., "Tissue Reaction to Three Ceramics of Porous and Non-Porous Structures," *J. Biomed. Mater. Res* 6, 347-374 (1972); V. Sollazzo, et al., "Zirconium oxide coating improves implant osseointegration in vivo," *Dent Mater* 24, 357-361 (2008); T. Tasdemir, et al., "Evaluation of the radiopacity of new root canal paste/sealers by digital radiography," *Journal of endodontics* 34, 1388-1390 (2008); M. A. Duarte, M. A., et al., "Influence of calcium hydroxide association on the physical properties of AH Plus," *Journal of endodontics* 36, 1048-1051 (2010); A. L. G. Cornelio, et al., "Cytotoxicity of Portland Cement with Different Radiopacifying Agents: A Cell Death Study," *J. Endodontics* 37, 203-210 (2011); F. M. Collares, et al., "Nanostructured hydroxyapatite as filler for methacrylate-based root canal sealers," *Int Endod J* 45, 63-67 (2012)}

34, 1388-1390 (2008); M. A. Duarte, M. A., et al., "Influence of calcium hydroxide association on the physical properties of AH Plus," *Journal of endodontics* 36, 1048-1051 (2010)} However, the use of such radiopaque materials within temporary stable fillers (designed to inhibit particle settling) for X-ray-based diagnosis of periodontitis has not been reported.

B. Tailoring of Solid Particles and Biocompatible Fluids for Stable Suspension Fillers Because $CaWO_4$, $CaZrO_3$, and other oxides have densities greater than water, dispersions of such particles in water will tend to settle under the influence of gravity. In the regime of Stoke's flow (for Reynold's numbers <0.20), the terminal settling velocity of spherical particles in a suspension can be approximated with the equation {R. Clift, et al., *Bubbles, Drops, and Particles*, Academic Press, NY, 1978; A. R. Khan, et al., "Fluid-Particle Interactions and Flow Characteristics of Fluidized Beds and Settling Suspensions of Spherical Particles," *Chem. Eng. Comm.*, 78, 111-130 (1989)}:

$$V_s(\text{in cm/s}) = (1/18)(d^2)g(\rho_P - \rho_F)(1-C_P)^{4.8}/\eta \quad (2)$$

where d=particle diameter; g=gravitational acceleration (981 cm/s$^2$); $\rho_P$=particle density; $\rho_F$=fluid density; $C_P$=particle concentration (volume fraction); and $\eta$=dynamic fluid viscosity. As revealed by equation (2), the settling rate may be reduced by decreasing the particle size, increasing the particle loading, and/or increasing the density and viscosity of the fluid.

TABLE 1

Calculated absorption of dental X-rays by various oxides (i.e., values of $1 - (I_x/I_o)$ for x = 100 μm thickness).

| Material | Density, ρ | $\mu/\rho\|_{20\,keV}$ | $1 - (I_x/I_o)\|_{20\,KeV}$ | $\mu/\rho\|_{120\,keV}$ | $1 - (I_x/I_o)\|_{120\,keV}$ |
|---|---|---|---|---|---|
| HA | 3.15 g/cm$^3$ | 6.56 cm$^2$/g | 0.187 | 0.181 cm$^2$/g | 0.00570 |
| TiO$_2$ (anatase) | 3.89 g/cm$^3$ | 9.85 cm$^2$/g | 0.318 | 0.197 cm$^2$/g | 0.00762 |
| CaTiO$_3$ | 4.03 g/cm$^3$ | 9.74 cm$^2$/g | 0.325 | 0.198 cm$^2$/g | 0.00796 |
| CaZrO$_3$ | 4.62 g/cm$^3$ | 40.0 cm$^2$/g | 0.842 | 0.461 cm$^2$/g | 0.0211 |
| CaWO$_4$ | 6.12 g/cm$^3$ | 44.0 cm$^2$/g | 0.932 | 2.17 cm$^2$/g | 0.124 |
| NaI$_{60}$H$_2$O$_{40}$ | 1.92 g/cm$^3$ | 13.4 cm$^2$/g | 0.227 | 0.812 cm$^2$/g | 0.0155 |

As shown in Table 1, $CaWO_4$ and $CaZrO_3$ should be appreciably more radiopaque than hydroxyapatite; that is, 100 μm of $CaWO_4$ and 100 μm of $CaZrO_3$ should absorb 93.2% and 84.2% of 20 keV dental X-rays, respectively, as opposed to 18.7% for $Ca_{10}(PO_4)_6(OH)_2$, and an even larger difference in X-ray absorption is expected for 120 keV X-rays.

MicroCT images (using a 50 kV Skyscan unit) quantitatively and qualitatively reveal the relative gray scale values (FIG. 1C) and radiopacities (FIG. 1D) of such oxide particles. For these images, mixtures of 40 wt % oxide powder (all with particle sizes of 54±10 μm diameter) in water were drawn into micropipette tips which were then sealed at both ends. The MicroCT images reveal the notably enhanced X-ray radiopacity of the $CaWO_4$ (lane 3 in FIG. 1D) and $CaZrO_3$ particles (lane 1 in FIG. 1D) relative to the other particles ($CaTiO_3$ in lane 2, $TiO_2$ in lane 4, and $Ca_{10}(PO_4)_6(OH)_2$ in lane 5 of FIG. 1D), consistent with the calculated values in Table 1. Indeed, owing to its enhanced radiopacity, calcium tungstate is currently used as a biocompatible radiopaque constituent in root canal sealers (e.g., Ah Plus® Root Canal Sealer, Dentsply De Trey GmbH). {T. Tasdemir, et al., "Evaluation of the radiopacity of new root canal paste/sealers by digital radiography," *Journal of endodontics*

In some embodiments, the biocompatible fluid contains an additive to increase the viscosity of the solution beyond the viscosity of water so as to decrease the settling rate of oxide particles below that for water. One example of such an additive is glycerol. Glycerol (glycerin) is a biocompatible fluid (used in toothpaste {C. Ganss, et al., "Efficacy of the stannous ion and a biopolymer in toothpastes on enamel erosion/abrasion," *J. Dent.*, 40, 1036-1043 (2012); http://householdproducts.nlm.nih.gov/cgi-bin/household/brands?tbl=brands&id=16030335}) that shares complete mutual solubility with water. The viscosity of glycerol-water solutions can be tailored over 2 orders of magnitude (i.e., from $\eta$=0.695 cP for pure water to $\eta$=154 cP for pure glycerol at 37° C. {*Handbook of Chemistry and Physics*, CRC Press, Boca Raton, Fla., 2011-2012; D. Lan, et al. "Excess Molar Properties and Viscosities of Glycerol+Water System at 298.15 to 318.15 K," *Asian J. Chem.*, 25, 2709-2712 (2013)}).

In some embodiments, the biocompatible fluid in the filler is a gel-forming solution that exhibits reversible thermal gelation. Examples of such solutions are poloxamer-water solutions. One such poloxamer molecule is Poloxamer 407, P-407 (or Pluronic F-127®, BASF Corp.), which is a water-soluble block co-polymer exhibiting reversible thermal gelation. {I. R., Schmolka, "Artificial skin. I. Preparation and properties of pluronic F-127 gels for treatment of burns," *J. Biomed. Mater. Res.,* 6, 571-582 (1972); P. Wang, et al., "Kinetics of Sol-to-Gel Transition for Poloxamer Polyols," *J. Appl. Polymer Sci.,* 43, 283-292 (1991); R. K. Prud'homme, et al., "Structure and Rheology Studies of Poly(oxyethylene-osypropylene-oxyethylene) Aqueous Solution," *Langmuir,* 12, 4651-4659 (1996); C.-W. Cho, et al., "Thermorheologic Properties of Aqueous Solutions and Gels of Poloxamer 407," *Drug Dev. Ind. Pharm.,* 13, 1227-1232 (1997)} For example, a solution of 20 wt % P-407 in water at 15° C. is highly fluid. However, upon heating to 37° C., this solution will form a highly-viscous "ringing" gel with a viscosity of ~$1.5 \times 10^4$ cP at 37° C. {K. Kurumada, et al., "Viscosity Studies of Pluronic F127 in Aqueous Solution," *Prog. Colloid Polymer Sci.,* 123, 12-15 (2004).} Upon cooling to 15° C., the gel will convert back to a highly fluid solution. In one embodiment, chilled P-407-bearing solutions are used as biocompatible fluids in fillers containing X-ray radiopaque particles, such as $CaWO_4$. The P-407-bearing fillers will be fluid at 15° C. to allow for insertion into periodontal pockets via a syringe, and then set (at body temperature, 37° C., in the pockets) into highly-viscous (rigid) gels to inhibit $CaWO_4$ particle settling during imaging. After imaging, the fillers may be removed (e.g. by ultrasonic scaling) or left in place for gradual dissolution in saliva.

Calculated values of terminal settling velocity ($V_s$), and associated vertical settling distance in 5 min ($Z_{5min}$), for fillers containing 20 vol % $CaWO_4$ are shown in Table 2. (Note: such formulations should possess X-ray mass absorption coefficients >4 times that for hydroxyapatite.) Small settling distances of $Z_{5min}$<0.04 mm in 5 min can be achieved with dispersions of $CaWO_4$ particles of 2 micrometers ($\mu$m) diameter in 88 wt % glycerol at 37° C. (unlike for pure water, as indicated in Table 2) or with dispersions of 44 diameter $CaWO_4$ particles in gels of 20 vol % P-407 formed at 37° C.

shearing, however, the viscosity decreases to yield a suspension that can flow into periodontal pockets. Such transient gelation is particularly attractive for the disclosed dental fillers, in that the CNC-bearing suspension may be designed to flow during passage through a syringe into a periodontal pocket, and then gel while resting in the pocket to form a viscous suspension that inhibits particle settling.

CNCs are produced by using 64% sulfuric acid to hydrolyze the amorphous regions of cellulose polymers, leaving acid resistant crystals as a product. The other main by-product is glucose. The crystals are purified by diluting and neutralizing the acid and then separating the soluble components from the insoluble CNC. This can be accomplished by dilution and settling, filtration on a vacuum filter, or filtration in a membrane unit. The final stage involves removal of water using the membrane filtration system, which leaves a 5%-11.5% aqueous slurry that is viscous and quite stable for extended storage. The low water content and high ionic strength from the sulfuric acid groups on the CNCs limit bacterial or fungal growth in the suspension.

C. Solid Particles Derived by Coating of Templates with X-Ray Radiopaque Materials In another embodiment, the solid particles in the filler contain an X-ray radiopaque inorganic compound that is a coating deposited on a template in the form of a particle. The template can be a spherical particle, a non-spherical particle, an organic particle, or a combination thereof. The organic template particle can be or contain nanocellulose, a cellulose nanofiber (also called microfibrillated cellulose), nanocrystalline cellulose, bacterial nanocellulose, or a combination thereof.

In another embodiment, the template is an inorganic particle. For example, the template can be a biogenic inorganic particle. The biogenic inorganic particle template can be the $SiO_2$ microshell of a diatom. In another embodiment, the template is a synthetic inorganic particle.

As an example, the particle template is a cellulose nanocrystal (CNC). CNCs are composed of nanosized cellulose

TABLE 2

Calculated values of terminal settling velocity ($V_s$) and associated settling distances in 5 min ($Z_{5min}$) for $CaWO_4$-bearing suspensions (at 37° C.).

| Fluids | $\rho_F$ (g/cm$^3$) | $\eta$* (g/cm · s) | $C_P$ (vol %) | d ($\mu$m) | Re** | $V_s$ (mm/s) | $Z_{5min}$ (mm) |
|---|---|---|---|---|---|---|---|
| Water | 0.993 | 0.00695 | 20.0 | 2.0 | $1.6 \times 10^{-5}$ | $5.51 \times 10^{-3}$ | 1.7 |
| Glycerol (88 wt % in water) | 1.24 | 0.969 | 20.0 | 2.0 | $9.6 \times 10^{-10}$ | $3.76 \times 10^{-5}$ | 0.011 |
| P-407 (20 wt % in water) | 1.00 | 1.50 | 20.0 | 44 | $3.6 \times 10^{-10}$ | $1.23 \times 10^{-4}$ | 0.037 |

*A viscosity of 1 g/cm · s = 100 cP;
**Re = dimensionless Reynold's number = $\rho dV/\eta$
$\rho_F$ = fluid density,
$\eta$ = fluid viscosity,
$C_P$ = solid particle loading,
d = solid particle diameter,
Re = Reynolds number,
$V_s$ = calculated settling velocity (equation 2).

Figure 3:
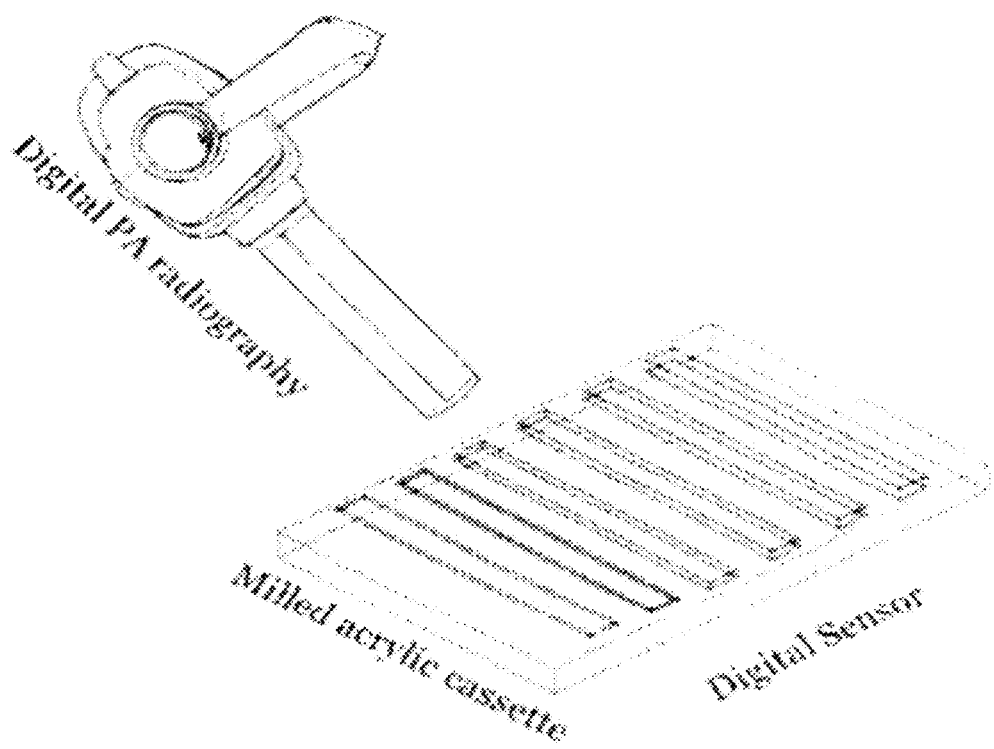
FIG. 3 is a partial cross sectional perspective view of the long cone paralleling technique for producing digital radiographs. Different formulations of filler material are expressed into the various channels of a milled acrylic cassette. Cassettes are then radiographed by digital periapical (PA) radiography.

In some embodiments, the biocompatible fluid in the filler is a thixotropic fluid. In one embodiment, the thixotropic fluid is a mixture of cellulose nanocrystals (CNCs) in water. Prior work has shown that aqueous suspensions of CNCs exhibit thixotropic behavior (Hasani, et al, *Soft Matter,* 4:2238-2244; 2008; Goff, et al., *J. Appl. Polym. Sci,* DOI: 10.1002/APP.40676; 2014; Liu, et al., *Dent. Mater.* 27:465-477; 2011). That is, in the absence of stirring/shearing, such suspensions gel to form a non-flowing suspension. Upon fibrils with a high aspect ratio (length to width ratio). Typical lateral dimensions are 5-20 nanometers and longitudinal dimensions are in a wide range from tens of nanometers to several micrometers. In one example, a scalable, automated surface sol-gel (SSG) process is used to apply coatings of X-ray radiopaque oxides of desired thickness to CNCs, as illustrated in FIG. 3. In order to generate a continuous and conformal oxide layer via the SSG process, the substrate should contain a high density of hydroxyl groups (FIG. 2A).

The hydroxyl-rich nature of CNC surfaces is particularly attractive for the SSG process, as no further amplification of the surface —OH concentration is likely to be necessary. Exposure of such hydroxyl groups to a metal alkoxide results in the formation of metal-oxygen bonds (FIG. 2B) and alcohol (not shown) as reaction products. Once a monolayer is deposited, the pendant, unreacted alkoxide (OR) groups may be exposed to water to regenerate bound hydroxyl (OH) groups, as well as alcohol product molecules, as illustrated in FIG. 2C. Hence, repeated, alternating exposure to solutions of metal alkoxide and then water can be used to build up, in a layer-by-layer fashion, oxide layers of desired thickness (FIG. 2D).

In one example, the OH-rich surfaces of CNCs are exposed in an alternating fashion to a calcium alkoxide or a tungsten alkoxide solution and then to water, to allow for the layer-by-layer buildup of Ca—O and W—O layers in an appropriate stoichiometric ratio for the desired calcium tungstate compound (i.e., Ca:W=1:1 for $CaWO_4$). After depositing a Ca—W—O coating of desired thickness via use of an appropriate number of alkoxide/water cycles, the coated CNCs is exposed to thermal or hydrothermal conditions to allow for the formation of the desired crystalline calcium tungstate compound.

D. Methods of Making Dental Filler Compositions

1. Hydroxyapatite Suspensions in Glycerol

Hydroxyapatite suspensions in 70% glycerol solution were prepared by mixing appropriate amount of glycerol and deionized water. The 70% glycerol solution was then added to appropriate weights of hydroxyapatite {<0.2 μM particle size (BET), 97% purity; Sigma Aldrich} and mixed thoroughly by a combination of vortexing and sonication to make 20 wt %, 30 wt %, and 40 wt % of hydroxyapatite in 70% glycerol solution, resulting in an evenly distributed suspension.

2. Calcium Tungstate Suspensions in Glycerol

60% glycerol solution was prepared by mixing appropriate amount of glycerol and deionized water. The 60% glycerol solution was then added to the different oxides (calcium tungsten oxide, calcium zirconate, and calcium titanate, titanium oxide) to make 40 wt % suspensions. All the oxides were purchased from Alfa Aesar and were <45 micrometer particle in size and 98% purity.

III. Applications

A. Radiographic Approaches

Conventional Dental Digital Radiography

Digital radiography is a form of X-Ray imaging, where digital X-Ray sensors are used instead of traditional photographic film. A digital image capture device is used, which allows for immediate image preview and availability, elimination of costly film processing steps, a wider dynamic range, which makes it more forgiving for over- and under-exposure, as well as the ability to apply special image processing techniques that enhance overall display of the image. Other advantages include the ability to digitally transfer and enhance images as well as the need for less radiation to produce an image of similar contrast to conventional radiography.

In a preferred embodiment, the digital radiography is carried out using the long cone paralleling technique, where the film is placed parallel to the long axis of the tooth in question and the central X-Ray beam is directed perpendicular to the long axis of the tooth.

Micro-Computed Tomography (Micro-CT) Digital Radiography

This technique uses X-Rays to create microscopic cross-sections of a physical object that can be used to recreate a virtual model without destroying the original object. Two imaging systems within this category are cone beam reconstruction and fan beam reconstruction. Cone beam reconstruction uses a two-dimensional approach for obtaining projection data. Instead of utilizing a single row of detectors, as fan beam methods do, a cone beam system uses a standard charge-coupled device camera, focused on a scintillator material. The scintillator converts X-Ray radiation to visible light, which is picked up by the camera and recorded. The method is widely implemented in micro-tomography, and is also used in larger scale systems. An X-Ray source is positioned across from the detector, with the object being scanned in between. This is essentially the same setup used for an ordinary X-Ray fluoroscope. Projections from different angles are obtained in one of two ways. In one method, the object being scanned is rotated. This has the advantage of simplicity in implementation, since a rotating stage results in little complexity. The second method involves rotating the X-Ray source and camera around the object, as is done in ordinary CT scanning and single-photon emission computerized tomography (SPECT) imaging. This adds complexity, size and cost to the system, but removes the need to rotate the object.

The cone beam method is called as such because the X-Rays are emitted from the source as a cone-shaped beam. In other words, it begins as a tight beam at the source, and expands as it moves away. Prior work has revealed that micro-computed tomography produces radiographs with enhanced sensitivity and resolution (Liu, et al., *Dent. Mater.*, 27:465-477; 2011).

B. Exemplary Methods

In Vitro Evaluation of the Radiopacity of Biocompatible Fillers

Figures 7A, 7B, 7C, 7D, 7E, 7F:
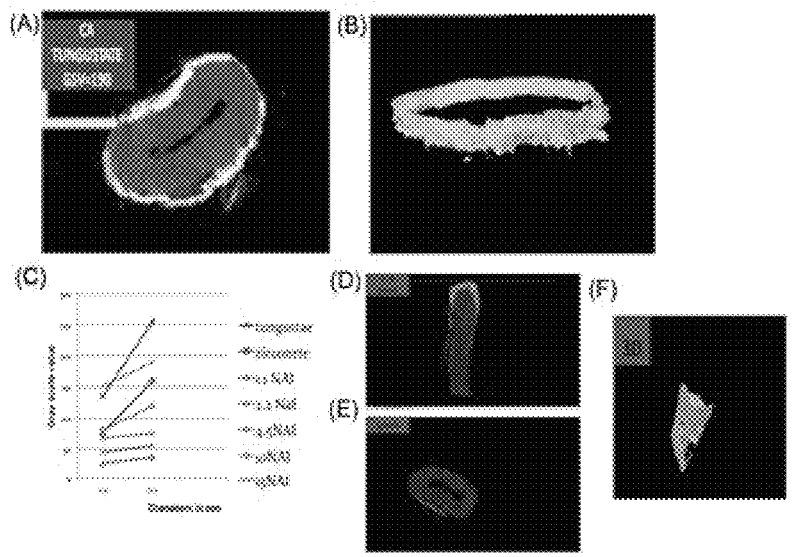
FIG. 7A is a three dimensional rendering of $CaWO_4$ (40% wt 0.5 microns CaWO4 in 60% glycerol) injected into the pocket of human tooth/Pig gingiva model=190.
FIG. 7B is a three dimensional rendering of a continuous pocket around tooth.
FIG. 7C is a graph of dimensions (mm) versus gray scale values of 1.1% wt NAI in 0.5 micron HA, 2.2% wt NAI in 0.5 micron HA, 4.5% wt in 0.5 micron HA, 10% wt NAI in 0.5 micron HA and 15% wt NAI in 0.5 micron HA relative to 40% wt 0.5 microns $CaWO_4$ or zirconate in 60% glycerol.
FIGS. 7D-7F are three dimensional renderings of prototypes if NaI in HA 15% wt NAI in HA solution.
Figures 8A, 8B, 8C, 8D, 8E:
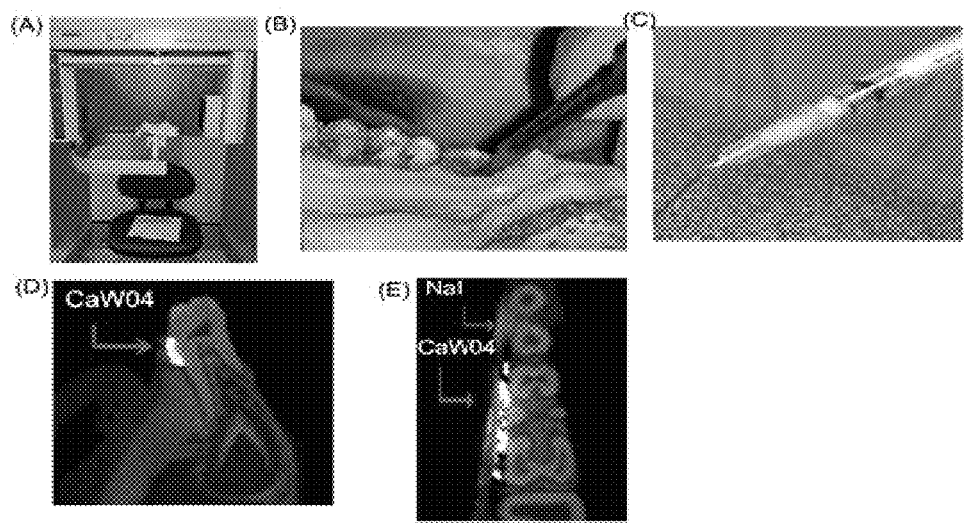
FIG. 8A is a photograph of a full sized Cone beam CT in a clinical setting to image the materials in a preserved pig jaw.
FIG. 8B is a photograph showing the formation of pockets using a scalpel. The pockets were injected with filler prototypes in glycerol and P-407 using a syringe FIG. 8C.
FIG. 8D is 2-D imaging of pig jaw by clinical CBCT showing marked radiopacity or brightness of $CaWO_4$ in pockets (FIG. 8D).
FIG. 8E is a 2-D imaging of pig jaw by clinical CBCT showing difference between NaI and $CaWO_4$ fillers.
Figures 9A, 9B, 9C, 9D, 9E, 9F:
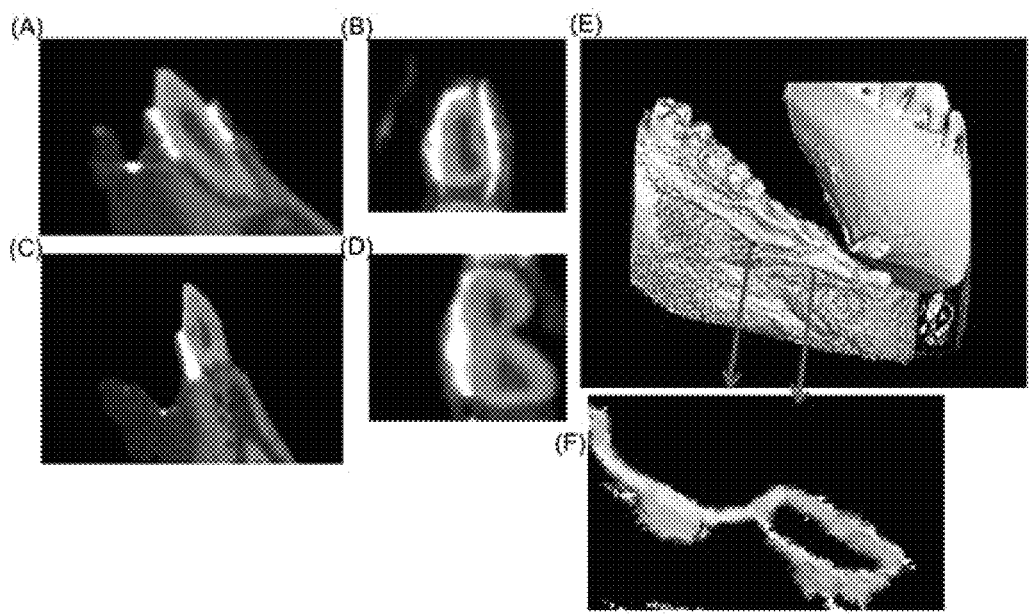
FIGS. 9A-9F are cone beam computed tomography imaging (CBCT) of periodontal pocket analogues in pig jaw. Combinations of $CaWO_4$ and NaI were injected into periodontal pockets in pig jaw, which was imaged in 2-D (FIGS. 9A-D) and 3-D (FIGS. 9E, F).

Five in vitro models will be used to evaluate the radiopacity of biocompatible fillers in 2D or 3D. For initial testing in 2D using long cone paralleling X-ray technique the custom milled blank acrylic plate model (FIG. 3) and the 96-well microtiter plate method shown in FIG. 1B will be used. Into the wells will be expressed different volumes of formulations of filler material. For further testing in 2D and 3D using the microCT, the human tooth/artificial gingiva model with created periodontal "pockets" (FIGS. 1E and 5) and a human tooth/pig gingiva model with created periodontal "pockets" (FIGS. 6 and 7). For further testing in 2D and 3D using a full-size clinical Cone Beam CT (CBCT) unit, an intact pig jaw in which periodontal pockets have been created with a scalpel will be used (FIGS. 8 and 9)

In some embodiments, the formulation contains diatom replica microparticles coated with $Ca_3P_2O_8$. In some embodiments, the formulation contains CNCs coated with $Ca_3P_2O_8$. In some embodiments, the formulation contains diatom replica microparticles coated with $Ca_{10}(PO_4)_6(OH)_2$. In some embodiments, the formulation contains CNCs coated with $Ca_{10}(PO_4)_6(OH)_2$. In different embodiments the layer-by-layer coatings are of varying thicknesses. In some embodiments, the formulation contains microparticles suspended in a glycerol-water solution. In different embodiments the glycerol-water solution is of varied compositions and viscosities to minimize particle settling within a given time. In different embodiments, the disclosed formulations contain different loadings of microparticles.

Each well of the plate will serve as a normalization control for its respective filled well. 96 well plates will be radiographed using the long cone paralleling technique and micro-CT at different time points, to determine average radiopacity, as well as microparticle settling kinetics. Computer-aided densitometry will be employed to develop a standard curve for each formulation, and linear regression analyses will be used to determine optimal formulations. Human tooth/gingiva models and pig jaw models will be used to evaluate the radiopacity of the formulations introduced into periodontal "pockets", then imaged in 2D and 3D using microCT or CBCT 3-D Imaging of Gels within Periodontal Pocket Analogues A real human dried skull with teeth, alveolar bone, and artificial "gingiva" will be utilized, along with cone beam CT as previously reported (Kalathingal, et al., *Oral Surg. Oral Med. Oral Pathol. Oral Radiol. Endod.*, 104:699-704; 2007)), in order to further develop the disclosed methods. Alveolar bone "defects" and furcation defects will be created with an end cutting dental bur. A line will be drawn around the CEJ of all the teeth, and a similar line will be applied to the base of the simulated "pocket". Probing depth measurements between the two lines will be conducted to serve as the gold standard. A lubricant will be applied between the two lines (from the CEJ to the base of the pocket) and cement will be applied apical to the bottom line (base of the pocket) to simulate the attachment apparatus. Polyvynil-siloxane will then be mixed and applied (1 mm average thickness) to simulate gingiva. After the gingiva has set, probing depth measurements will be made and compared to the gold standard to confirm the depth measurements.

This model will then be used in a cone beam CT (FIG. 4A) to determine the ability of various disclosed filler material formulations to accurately detect probing depth measurements. In some embodiments, the formulation will contain diatom replica microparticles coated with $Ca_3P_2O_8$. In some embodiments, the formulation will contain CNCs coated with $Ca_3P_2O_8$. In some embodiments, the formulation will contain diatom replica microparticles coated with $Ca_{10}(PO_4)_6(OH)_2$. In some embodiments, the formulation will contain CNCs coated with $Ca_{10}(PO_4)_6(OH)_2$. In different embodiments the layer-by-layer coatings will be of varying thicknesses. In some embodiments, the formulation will contain microparticles suspended in a glycerol-water solution. In different embodiments the glycerol-water solution will be of varied compositions and viscosities to minimize particle settling within a given time. In some embodiments, the disclosed formulations will contain different loadings of microparticles.

Pockets will be filled with a given filler material (FIG. 4B) using a syringe. A series of cone beam CT images will be utilized to generate a 3-D, digitally-reconstructed image of the periodontal pocket. It is anticipated that such a 3-D image will appear as a continuous ribbon around the teeth (FIGS. 4C, 7B, 9F), whose dimensions, surface area, and total volume can then be precisely evaluated as a function of total "disease exposure".

We claim:

1. A method for producing radiopaque particles comprising the steps of:
    (a) alternating exposure of OH-rich surfaces of cellulose particles to calcium alkoxide or tungsten alkoxide solution to allow for layer-by-layer buildup of Ca—O and W—O layers on the cellulose particles to a desired thickness; and
    (b) exposing the coated cellulose particles to thermal or hydrothermal conditions to allow for the formation of crystalline calcium tungstate particles.

2. The method of claim 1, wherein the radiopacity of the particles increases with increasing thickness of Ca—O and W—O layers on the cellulose particles.

3. The method of claim 1, wherein the cellulose particles are cellulose nanocrystals.

4. The method of claim 1, wherein the cellulose particles comprise microcrystalline cellulose, nanocellulose, cellulose nanofibers, bacterial nanocellulose, and combinations thereof.

* * * * *